United States Patent
Lu

Patent Number: 5,707,398
Date of Patent: Jan. 13, 1998

[54] AUTOMATIC DETERMINATION OF OPTIMUM ELECTRODE CONFIGURATION FOR A CARDIAC STIMULATOR

[75] Inventor: Richard Lu, Highlands Ranch, Colo.

[73] Assignee: Pacesetter, Inc., Sylmar, Calif.

[21] Appl. No.: 748,131

[22] Filed: Nov. 12, 1996

[51] Int. Cl.⁶ .................................................. A61N 1/00
[52] U.S. Cl. .................................................. 607/27; 607/24
[58] Field of Search ........................... 607/24, 27, 21, 607/22, 15, 18

[56] References Cited

U.S. PATENT DOCUMENTS

| | | |
|---|---|---|
| 4,549,548 | 10/1985 | Wittkampf et al. ................. 607/27 |
| 4,628,934 | 12/1986 | Pohndorf et al. .................. 607/27 |
| 4,901,725 | 2/1990 | Nappholz . |
| 5,003,975 | 4/1991 | Hafelfinger et al. ............... 607/27 |
| 5,097,831 | 3/1992 | Lekholm ............................ 607/24 |
| 5,441,523 | 8/1995 | Nappholz . |
| 5,562,712 | 10/1996 | Steinhaus . |

*Primary Examiner*—Scott Getzow
*Attorney, Agent, or Firm*—Gottlieb, Rackman & Reisman

[57] ABSTRACT

In an implantable pacemaker or cardioversion/defibrillation device, the optimal electrodes for determining a pacing parameter are found. A test signal is sequentially switched and a response from each of the remaining electrodes is determined. From those responses an optimal electrode or electrode pair is selected and used for pacing parameter determination. If an optimal electrode (a pair) is not found, then a fall back pacing rate is used.

17 Claims, 5 Drawing Sheets

5,707,398

AUTOMATIC DETERMINATION OF OPTIMUM ELECTRODE CONFIGURATION FOR A CARDIAC STIMULATOR

FIELD OF THE INVENTION

This invention relates to implantable cardiac pacemakers and defibrillators and, more particularly, to a method and apparatus in such a pacemaker for determining the optimal electrode pair for measuring a metabolic parameter such as minute volume used for metabolic rate response.

BACKGROUND OF THE INVENTION

Cardiac pacemakers stimulate a patient's heart by applying current pulses to cardiac tissues via two electrodes, a cathode and an anode. Standard pacing leads are available in either of two configurations, unipolar leads or bipolar leads, depending on the arrangement of the electrodes of a particular lead. A unipolar pacing lead contains a single electrode, normally the cathode, which extends perveneously distal from the pacemaker in an insulating enclosure until it is adjacent to the tip of the lead where the insulation is terminated to provide for electrical contact of the cathode with the heart tissue. The anode provides a return path for the pacing electrical circuit. For a unipolar lead, the anode is the pacemaker case. A bipolar lead contains two electrodes within an insulating sheath, an anode which extends distal from the pacemaker to a position adjacent to, but spaced from, the electrode tip, and a cathode which also extends distal from the pacemaker, but terminates a short distance distal of the anode, at the lead tip. The anode commonly takes the form of a ring. The cathode and anode of a bipolar lead are separated by an insulating barrier. In present-day pacemakers, circuits for pacing and sensing, which determine tip, ring and case electrode connections, are provided. Thus, the pacemakers can be programmed via telemetry for either bipolar or unipolar operation with respect to either sensing or pacing operations.

In rate responsive pacemakers, a metabolic parameter is also determined by making measurements through the electrodes and this parameter is then used a pacing rate corresponding to the metabolic demand of the patient. For example, in pacemakers made by the assignee of the present invention, the metabolic parameter is the minute volume, as described in U.S. Pat. No. 4,901,725, entitled "Minute Volume Rate-Responsive Pacemaker", issued to T. A. Nappholz et al. on Feb. 20, 1990. Minute volume may be determined by injecting a current between one electrode and the pacemaker case and measuring the impedance between another electrode and the case. More particularly, in conventional electrode configurations used for MV measurements, a current is injected between the ventricular ring and the pacemaker case and impedance measurements are then made between the ventricular tip and the pacemaker case by determining the respective transthoracic impedance. Therefore, in this mode of operation a bipolar lead is required in the ventricle.

Alternatively, a rate responsive pacemaker may be used with dual unipolar electrodes, as described in commonly assigned application Ser. No. 08/345,651, now U.S. Pat. No. 5,562,712, entitled "Minute Volume Rate-Responsive Pacemaker Using Unipolar Leads", incorporated herein by reference, wherein current is injected between the tip of the unipolar atrial lead and the case and the impedance is measured between the tip of the ventricular lead and the case. In both configurations, the reliability of the MV measurements is not evaluated by the pacemaker. Therefore, an inappropriate pacing rate may result if the MV signal is erroneous, due for example, to a broken lead or an improperly positioned electrode, or a lead with an intermittent connection.

OBJECTIVES AND SUMMARY OF THE INVENTION

Therefore it is an objective of the present invention to provide a cardiac pacing system wherein a metabolic parameter is measured using several electrode pairs and a decision is made automatically to select the pair which provides optimal performance.

A further objective is to provide a rate responsive pacemaker which verifies the operation of the electrodes at regular intervals, and which reverts to a non-rate responsive mode if the metabolic parameter determination is found to be unreliable and no alternative electrodes can be found to provide appropriate operation.

A further objective is to provide an improved pacemaker without the above-disadvantages with minimal modifications in the existing rate responsive pacemakers.

Other objectives and advantages of the invention shall become apparent from the following description. Briefly, a pacemaker constructed in accordance with this invention includes a plurality of electrodes for sensing cardiac activity and for providing selective cardiac pacing, means for generating a metabolic demand signal derived from said electrodes, and means for selecting the optimal electrodes for said metabolic demand indication signal by testing the signals sensed in said electrodes. If none of signals derived from the electrodes are satisfactory for MV measurement, a fall-back scheme is used wherein the metabolic demand indication signal is ignored and pacing pulses are delivered through the most reliable pairs of electrodes at a predetermined rate. In a further embodiment, the electrodes of a defibrillator/pacemaker may also be used.

DETAILED DESCRIPTION OF THE INVENTION

Figure 1:
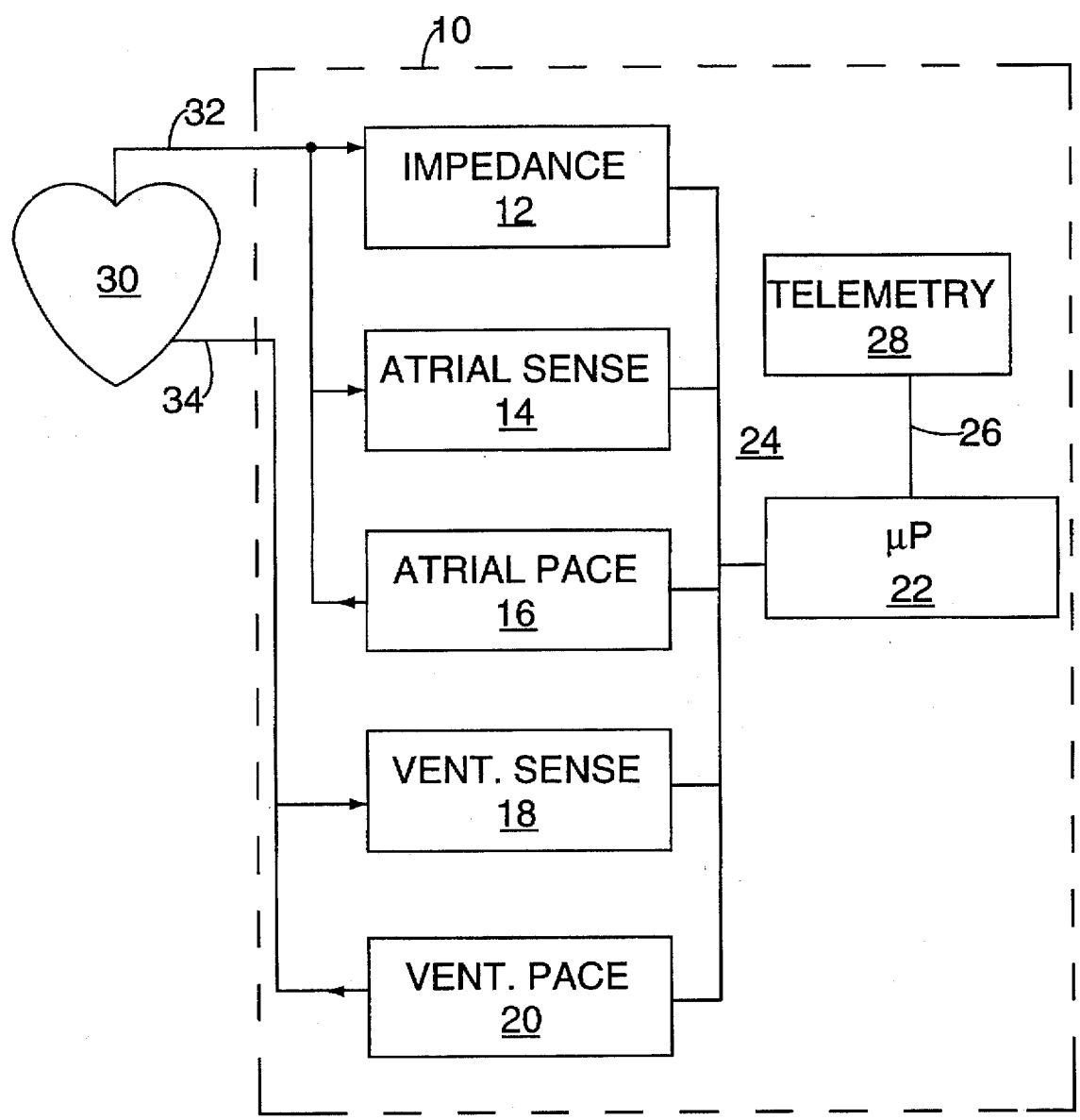
FIG. 1 shows a block diagram for a pacemaker constructed in accordance with this invention.

Referring now to FIG. 1, an implantable pacemaker 10 constructed in accordance with this invention includes an impedance circuit 12, an atrial sense circuit 14, an atrial pace circuit 16, a ventricular sense circuit 18 and a ventricular pace circuit 20. These circuits are connected to a microprocessor 22 by a bus 24. The microprocessor 22 is further connected by another bus 26 to a telemetry circuit 28. The pacemaker is connected to the heart 30 of a patient by two bipolar leads, atrial lead 32 and ventricular lead 34. In this embodiment, the pacemaker 10 is operated in a dual chamber mode, and in this mode it senses cardiac activity in the atrium and ventricle of the heart 30 via the bipolar leads 32, 34. The pacemaker 10 further senses through these electrodes, as described more fully below, an impedance indicative of the metabolic demand of the patient. The microprocessor process the information descriptive of the cardiac activity and the impedance and, when required, generates cardiac pacing pulse commands to the pace circuits 16 and 20. These circuits then generate appropriate pacing pulses. Details of this operation are described for example, in U.S. Pat. No. 5,441,523, incorporated herein by reference.

Figure 2:
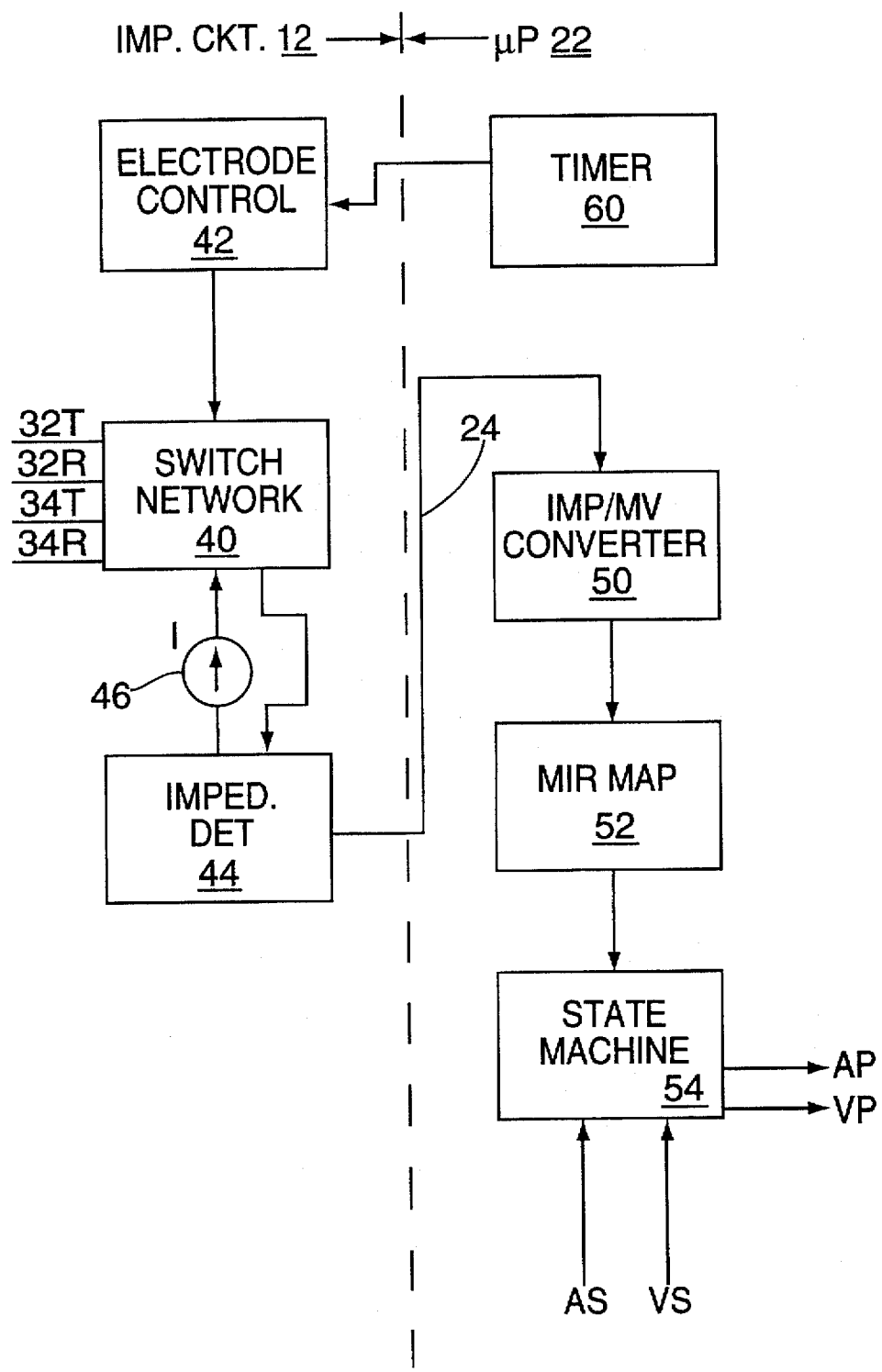
FIG. 2 shows a block diagram for impedance circuit of FIG. 1 as well as relevant portions of the microprocessor.

Typically, in the prior art, the impedance circuit was coupled to one of the leads. For example, in the above-mentioned U.S. Pat. No. 5,441,523 the impedance measurement was made using the ventricular lead. However, as described above, because of problems with one or both electrodes of these leads, the impedance circuit 12 may not derive a proper metabolic demand signal. In order to overcome his problem, the present invention is arranged and constructed to allow the impedance circuit 12 to determine the metabolic demand by making other measurements. More particularly, as seen in FIG. 2, the impedance circuit 12 includes a switch network 40, an electrode selection control 42, an impedance determinator circuit 44 and a current source 46. The switch network 40 is connected to the atrial tip electrode 32T and the atrial ring electrode 32R by lead 32, the ventricular ring electrode 34R and the ventricular tip electrode 34T by lead 34. In order to make an impedance measurement, in response to control signals from electrode control 42, the switch network 40 applies a current from current source 46 to one of the electrodes and the parameter case, and provides the response sensed between another of the electrodes and the pacemaker casing to impedance determinator 44. The determinator 44 then generates an impedance parameter indicative of this impedance. The impedance parameter is sent to the microprocessor 22 via bus 24.

The microprocessor 22 includes an impedance/minute volume converter 50 to generate for each impedance parameter a corresponding MV parameter. The MV parameter is transmitted to a mapping circuit 52 which convert the MV into a corresponding metabolic indicated rate, MIR. The MIR is fed to a state machine 54. The state machine 54 also receives as inputs, the atrial and ventriculars sense signals AS and VS from the atrial sen circuit 14 and the ventricular sense circuit 18, respectively. The state machine 54 generates, when required, atrial pulse commands AP and ventricular pulse commands VP for the atrial and ventricular pace circuits 16, 20, respectively.

Figure 3:
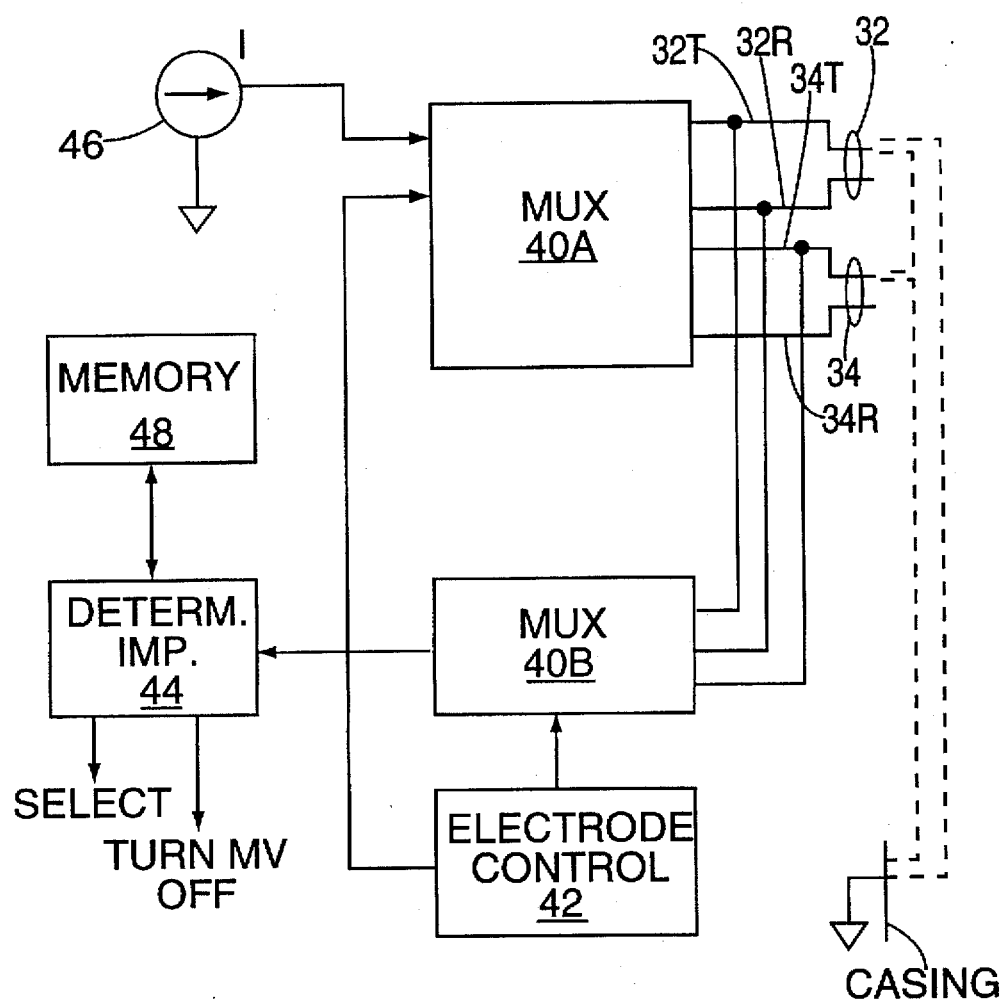
FIG. 3 shows details of the impedance circuit.

Referring now to FIG. 3, the switching network 40 consists of a multiplexer 40A and a demultiplexer 40B. These are connected to the four electrodes 32T, 32R, 34T, 34R as shown. The multiplexer 40A receives its input from the current source 46. The output of demultiplexer 40B is fed to impedance determinator 44. The determinator 44 stores readings from the electrodes into a memory 48, as described below. Memory 48 may be part of the circuit 12 or may be a memory associates with microprocessor 22.

Figure 4:
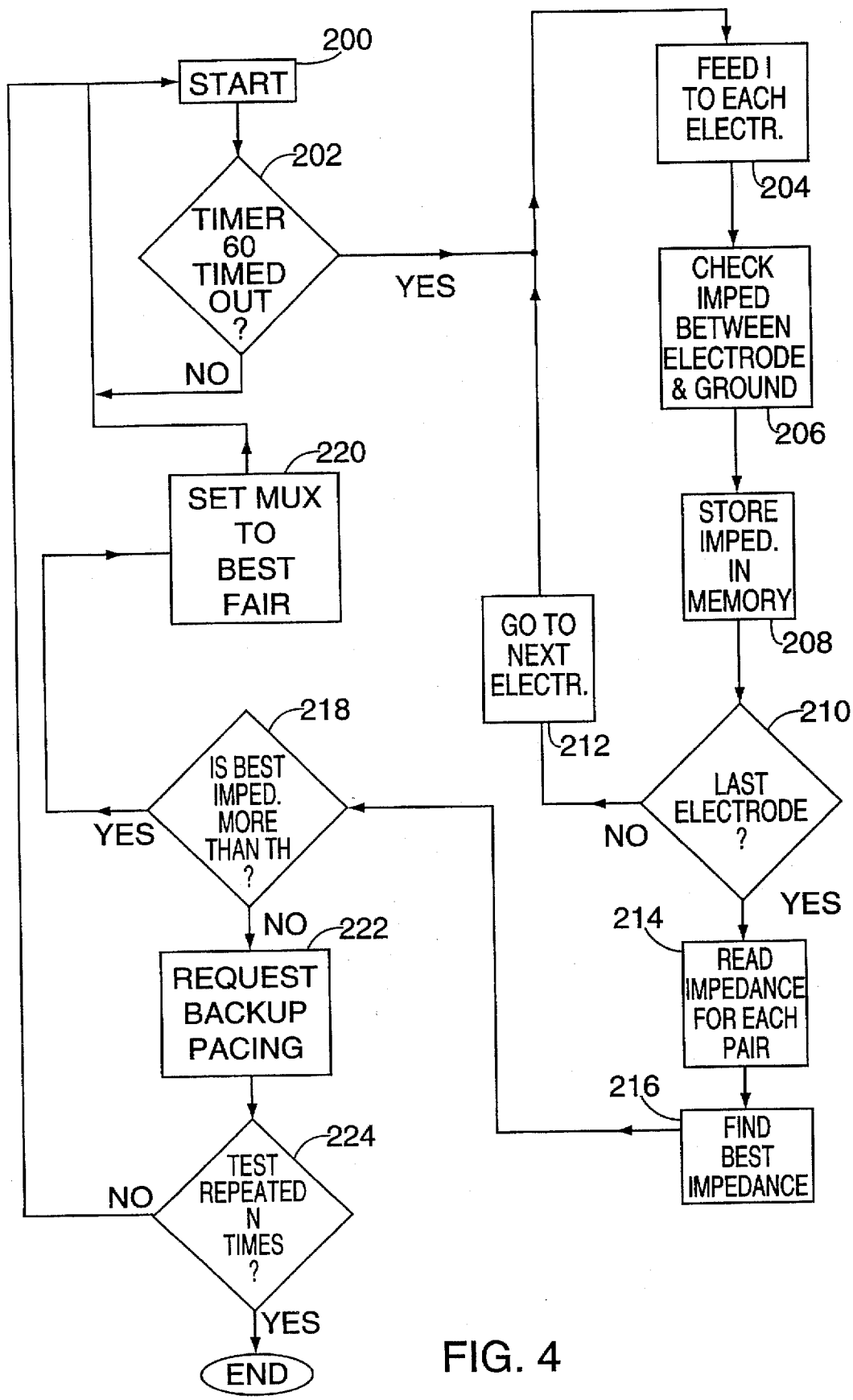
FIG. 4 shows a flow chart for the operation of the pacemaker.

The operation of the invention shall now be described in conjunction with the flow chart of FIG. 4. Initial programming values and other parameters are loaded into the microprocessor 22 during the initializing of the device (step 200). This initial set up also includes designation a preferred set of electrodes for the impedance measurement. For example, as discussed above, initially the impedance parameter may be measured by applying current to the ventricular ring electrode 34R. In other words, initially the electrode controller 42 sets the multiplexer 40A so that the current from source 46 flows to the electrode 34R. From this electrode 34R current flows through the cardiac tissues and across the pleural cavity to the casing 62 of pacemaker 10. Multiplexer 40B is set by controller 42 so that the ventricular tip electrode 34T is connected to the impedance determinator 44. The determinator 44 determines the corresponding transthoracic impedance as described above.

Following the set step 200, a timer 60 is initiated. After timer 60 times out (step 202) a signal is generated by the impedance determinator to perform a reliability check on the electrode system. The timer 60 may be set for example to initiate the reliability check every 30 days. This reliability check is performed as follows. In step 204 the multiplexer 40A is set to feed current I to a first electrode and all or some of the other electrodes are connected by the multiplexer 40B sequentially to obtain corresponding impedance measurements by impedance determinator 44 (step 206). The results are stored in step 208 into memory 48. In step 210 a check is performed as to whether the multiplexer 40A is at the last electrode. If not, than in step 212 the multiplexer 40A is advanced to the next electrode and steps 204–210 are repeated.

After all the data has been collected and stored in memory 48, then in step 214 the microprocessor 22 looks up all the impedance values and selects the best impedance value and the corresponding electrode pair that was the source of this value (step 216) determined in accordance with preselected criteria. In step 218 a check is performed to determine if the best value is above a certain preselected threshold TH. If it is, then in step 220 the multiplexer 40A and the multiplexer 40B are set to the pair of electrodes that resulted in the best impedance reading and then the process is started over again.

If in step 218 it is determined that even the best impedance value is too low, then in step 222 a signal is sent to the state machine 54 to turn the rate responsive feature off and to pace at a preselected standby rate. This mode is continued for a preselected time after which the reliability check is repeated. This may be continued until a suitable electrode pair is found or suspended after a suitable electrode pair cannot be found for n (e.g., 5) times (step 224).

Figure 5:
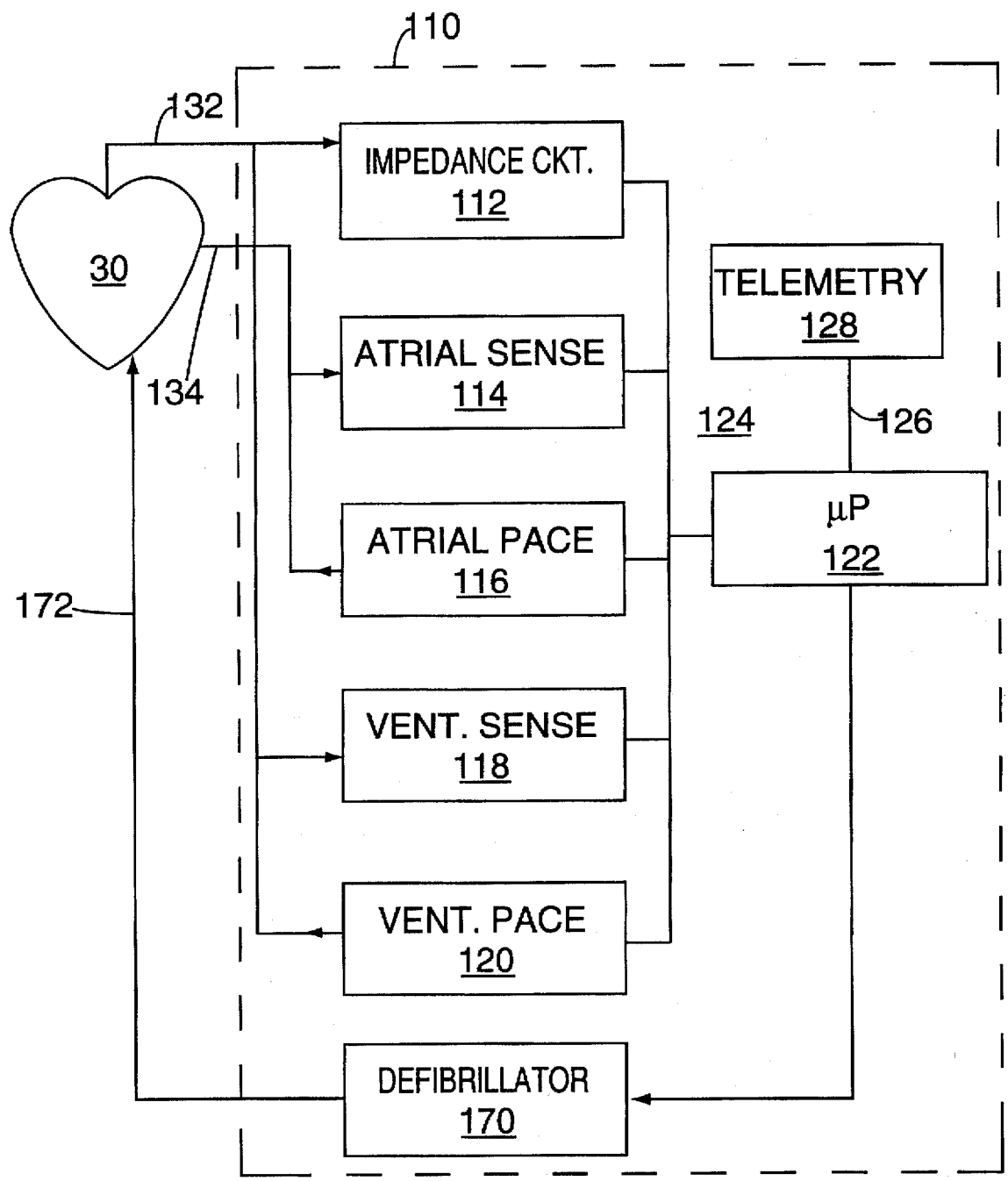
FIG. 5 shows a cardioverter/defibrillator constructed in accordance with the present invention.

FIG. 5 shows another embodiment invention. In this embodiment an implantable cardioversion/defibrillation device 110 is provided consisting of impedance circuit 112, atrial sense circuit 114, atrial pace circuit 116, ventricular sense circuit 118, ventricular pace circuit 120, microprocessor 122, bus 124, bus 126, telemetry circuit 128 and defibrillator 170. Device 110 is coupled to the heart 30 via electrodes 132, 134 and 172. The elements of FIG. 5 which are common to pacemaker 10 operate in the manner described above.

The cardioversion/defibrillator circuit 170 is controlled by microprocessor 122 to generate defibrillator pulses to electrode(s) 172. Advantageously, the electrode(s) 172 is also connected to the impedance circuit 112. The multiplexer 40A and multiplexer 40B are modified to accept an extra connection from this electrode 172. In this manner, the impedance circuit is able to determine impedance readings not only from the atrial and ventricular leads but also through the defibrillation lead(s).

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

I claim:

1. A rate responsive implantable pacemaker comprising:
a sensor sensing electrical activity in the heart and generating corresponding sense signals;
a pace generator generating pacing pulses to said heart in response to commands;
a plurality of electrodes for providing signals indicative of said electrical activity to said sensor, delivering pacing signals to said heart from said pace generator and performing a metabolic measurement;
a metabolic parameter generator generating a metabolic parameter indicative of a metabolic demand of said patient from said metabolic measurement;
a controller receiving said sense signals, and said metabolic parameter and generating in response said commands; and
an electrode selector selecting an optimized set of electrodes from said plurality of electrodes for performing said metabolic measurement.

2. The pacemaker of claim 1 wherein said plurality of electrodes includes an atrial electrode lead and ventricular electrode lead.

3. The pacemaker of claim 1 wherein said electrodes each include a tip and a ring electrode.

4. The pacemaker of claim 1 wherein said electrode selector includes impedance detector for determining impedances based on said selected electrodes.

5. The pacemaker of claim 4 wherein said detector determines a transthoracic impedance related to said metabolic demand.

6. An implantable cardiac device comprising:
an atrial electrode lead terminating in an atrial tip and an atrial ring electrode;
a ventricular electrode lead terminating in a ventricular tip electrode and a ventricular ring electrode;
sensor circuitry for sensing atrial and ventricular activity;
pacing circuitry for generating atrial and ventricular paces in response to commands;
a controller in communication with said sensor circuitry for generating said commands in response to a pacing parameter;
a parameter circuit for generating said pacing parameter in response to signals received from at least one of said electrodes, said pacing parameter being dependent on a metabolic demand of said patient; and
an electrode selector for selecting an optimal electrode from said electrodes for generating said pacing parameter and for connecting said optimal electrode to said parameter circuit.

7. The device of claim 6 wherein selector includes a tester for testing each of said electrodes and a determinator for determining said optimal electrode pair from said electrodes.

8. The device of claim 6 wherein said selector includes a source for a test signal, a first switch for connecting said test signal sequentially to each of said electrodes and a determinator for determining a response to said test signal.

9. The device of claim 8 wherein said selector further includes a second switch for connecting said determinator sequentially to each of said electrodes to detect said response.

10. The device of claim 6 wherein said metabolic demand is a minute volume.

11. The device of claim 6 wherein said pacing parameter is determined from a transthoracic impedance.

12. The device of claim 6 wherein said device is a cardioverter/defibrillator and further includes a defibrillator electrode.

13. In a dual chamber implantable cardiac device having atrial and ventricular leads each terminating in respective tip and ring electrodes, sensor circuitry for sensing cardiac activity, pacing circuitry for generating cardiac pacing signals and a pacing parameter calculator for generating a pacing command based on a metabolic demand of a patient, a method of determining an optimal electrode for said pacing parameter calculator, said method comprising the steps of:
generating a test signal;
applying said test signal sequentially to said electrodes;
detecting corresponding responses to said test signal, using a response detector;
selecting an optimal response from said responses; and
connecting an optimal electrode corresponding to said optimal response to said pacing parameter calculator.

14. The method of claim 13 further comprising sequentially connecting said response detector to said electrodes to detect said responses.

15. The method of claim 13 wherein said response detector determines an impedance.

16. The method of claim 13 wherein said device is a cardioverter/defibrillator including a defibrillator electrode further comprising the steps of:
applying said test signal to said defibrillator electrode; and
detecting a response to said test signal.

17. The method of claim 13 further comprising the steps of:
comparing the optimal response to a threshold level; and
if the optimal response does not meet a preset criteria with respect to said threshold level, generating pacing pulses at a backup rate.

* * * * *